United States Patent
Ben Nun

(10) Patent No.: US 10,507,007 B2
(45) Date of Patent: Dec. 17, 2019

(54) OPHTHALMIC ULTRASOUND BIO-MICROSCOPE (UBM) APPARATUS

(71) Applicants: Dov Helbetz, Herzliya (IL); Joshua Ben Nun, Beit Herut (IL)

(72) Inventor: Joshua Ben Nun, Beit Herut (IL)

(73) Assignee: Dov Helbetz, Herzliya (IL)

( * ) Notice: Subject to any disclaimer, the term of this patent is extended or adjusted under 35 U.S.C. 154(b) by 0 days.

(21) Appl. No.: 16/308,916

(22) PCT Filed: Jun. 13, 2016

(86) PCT No.: PCT/IL2016/050619
§ 371 (c)(1),
(2) Date: Dec. 11, 2018

(87) PCT Pub. No.: WO2016/203465
PCT Pub. Date: Dec. 22, 2016

(65) Prior Publication Data
US 2019/0150886 A1   May 23, 2019

(51) Int. Cl.
*A61B 8/00* (2006.01)
*A61B 8/10* (2006.01)
*A61B 3/00* (2006.01)
*A61B 3/13* (2006.01)

(52) U.S. Cl.
CPC .............. *A61B 8/10* (2013.01); *A61B 3/0008* (2013.01); *A61B 3/0075* (2013.01); *A61B 3/0091* (2013.01); *A61B 3/13* (2013.01); *A61B 8/4245* (2013.01); *A61B 8/4461* (2013.01)

(58) Field of Classification Search
CPC ....... A61B 3/0075; A61B 3/13; A61B 3/0008; A61B 3/0025; A61B 3/0058; A61B 3/0091; A61B 3/10; A61B 3/117; A61B 3/14; A61B 8/10; A61B 8/42; A61B 8/4218; A61B 8/4245; A61B 8/4461
See application file for complete search history.

(56) References Cited

U.S. PATENT DOCUMENTS

| 5,347,331 | A | 9/1994 | Isogai |
| 5,562,095 | A * | 10/1996 | Downey .................. A61B 8/12 600/445 |
| 5,776,068 | A | 7/1998 | Silverman et al. |
| 6,053,614 | A | 4/2000 | Kawamura et al. |
| 6,837,855 | B1 | 1/2005 | Puech |
| 7,224,822 | B2 | 5/2007 | Heacock |

(Continued)

FOREIGN PATENT DOCUMENTS

| CN | 201743710 U | 2/2011 |
| WO | 2013159076 | 10/2013 |
| WO | 2013185784 | 12/2013 |

*Primary Examiner* — Jordan M Schwartz
(74) *Attorney, Agent, or Firm* — ISUS Intellectual Property PLL; Anthony Jason Mirabito

(57) ABSTRACT

Ophthalmic Ultrasound Bio-Microscope (UBM) apparatus for eye examinations of a human subject in a supine position and fixating the gaze of his examined eye on an illuminated overhead fixation target. The ophthalmic UBM apparatus has a vertical UBM examination centerline on which overhead fixation target is located therealong and a UBM scanner with a UBM probe directed towards an examined eye at a known spatial position with respect to the overhead fixation target for acquisition of UBM scans of fixated examined eyes.

10 Claims, 11 Drawing Sheets

(56) References Cited

U.S. PATENT DOCUMENTS

| | | |
|---|---|---|
| 2008/0200807 A1* | 8/2008 | Wright ................... A61B 8/10 600/443 |
| 2008/0212029 A1* | 9/2008 | Ichikawa ............. A61B 3/0041 351/208 |
| 2009/0192389 A1 | 7/2009 | Eilers et al. |
| 2010/0004538 A1 | 1/2010 | Eilers et al. |
| 2010/0249562 A1 | 9/2010 | Zhang |
| 2012/0274903 A1 | 11/2012 | Sayeram et al. |
| 2013/0050645 A1* | 2/2013 | Sato ........................ A61B 3/13 351/206 |
| 2013/0141696 A1 | 6/2013 | Gertner et al. |

* cited by examiner

OPHTHALMIC ULTRASOUND BIO-MICROSCOPE (UBM) APPARATUS

FIELD OF THE INVENTION

This invention relates to ophthalmic ultrasonography in general and ophthalmic ultrasound bio-microscopy in particular.

BACKGROUND OF THE INVENTION

Conventional Ophthalmic Ultrasound Bio-Microscope (UBM) apparatus includes a UBM scanner having a hand manipulated single UBM probe with a single UBM transducer for in vivo eye examinations for a wide range of clinical applications. The UBM probe can be optionally mounted on an articulated arm for supporting its weight. UBM probes typically operate either at 35 MHz frequency or 50 MHz frequency for anterior segment imaging purposes. Such UBM probes are capable of acquiring UBM scan resolutions of about 25 µm axial resolution and about 100 µm lateral resolution. Higher frequency UBM probes at over 80 MHz are also available for imaging superficial pathologies or anatomical structures such as, Schlemm's canal, and the like. Some UBM probes are provided with interchangeable UBM transducers.

One particular clinical application of UBM scanners is facilitating positioning of one type of intraocular lenses intended for posterior chamber implantation, namely, so-called Intraocular Contact Lenses (ICLs). IntraOcular Lenses (IOLs) designed for posterior chamber implantation are commonly classified into the following three main categories each presenting its own challenges regarding selection, design and positioning:

First, so-called phakic IOL considered to be Intraocular Contact Lenses (ICLs) deployed between an iris and a crystalline lens by ciliary sulcus support. The distance between an ICL's posterior surface and a crystalline lens's anterior capsule is required to greater than 250 µm and smaller than 750 µm. Positioning an ICL too close to a crystalline lens less than 250 µm can result in friction leading to the formation of a cataract at its points of contact. Against that, positioning an ICL too forward might urge an ICL into an anterior chamber possibly leading to pupillary block glaucoma and/or damage to a corneal endothelium. The correct positioning of ICLs is even more difficult and critical when they are also being used for correction of astigmatism. At present, the estimated percentage of positioning related complications is about 15% including cataract formation and optical errors related to inadequate positioning.

Second, pseudophakic IOLs for implantation inside a vacated capsular bag (so-called in the bag IOLs) as a sequential step after removal of a cataractous crystalline lens. For pseudophakic IOLs, the challenges include the ability to calculate a required optical power of an implanted IOL to provide optimal vision correction and predict an accurate IOL position in a capsular bag and hence the optimal location of an IOL along an implanted eye's visual axis. This optimal location is a result of a force balance between an IOL and a capsular bag with all its zonuli attached. The key for accurate IOL power calculation is the ability to analyze the equilibrium point between a capsular bag and an IOL to be implanted. At the present time, the optical power of IOLs currently implanted during cataract surgery is calculated using an estimated location of an implanted IOL inside a capsular bag. This estimated location is the source of optical deviation of the surgical outcome from optimal optical results.

And third, accommodating IOLs which are pseudophakic optomechanical devices designed to restore accommodation by being operated by a minute movement range provided by a capsular bag-zonuli-ciliary muscles complex. Accommodating IOLs have similar optical challenges as pseudophakic IOLs and in addition also require accurate mechanical adjustments with the ocular tissues which operate them.

There is a need to provide ophthalmic apparatus for use in a wide range of in vivo clinical applications. Such clinical applications include inter alia examination of anterior segment structures including eye wall structures, for example, Schlemm's canal, and the like. Also, the selection, design and positioning of the aforesaid three IOLs categories in human eyes.

SUMMARY OF THE INVENTION

Generally speaking, the present invention is directed towards Ophthalmic Ultrasound Bio-Microscope (UBM) apparatus including an UBM scanner for eye examinations of a human subject in a supine position and fixating the gaze of his examined eye on an illuminated overhead fixation target for fixation purposes. The ophthalmic UBM apparatus of the present invention includes a vertical UBM examination centerline on which the overhead fixation target is located therealong and a UBM scanner with a UBM probe directed towards an examined eye at a known spatial position with respect to the overhead fixation target for acquisition of UBM scans of fixated examined eyes. In greater particularity, the present invention is directed towards ophthalmic UBM apparatus for anterior segment examinations for enabling processing of vertical UBM scans to construct computerized vertical cross sections of anterior segments along clock time probe positions relative to the UBM examination centerline. The computerized vertical cross sections of anterior segments are combined from UBM scans acquired at diametric clock time probe positions, for example, 12:00 and 6:00, 3:00 and 9:00, and the like. Accordingly, the ophthalmic UBM apparatus of the present invention takes into consideration that while human eyes share a generally ovoid shape they have considerable individual morphological variability. Moreover, the ophthalmic UBM apparatus of the present invention enables construction of computerized 3D models of anterior segments from multiple computerized vertical anterior segment cross sections.

The ophthalmic UBM apparatus of the present invention employs the innate ability of an examined eye to fixate on an illuminated overhead fixation target and maintain fixation throughout an eye examination. Such gaze stability has been clinically approved and is widely employed during laser based refractive surgeries for corneal laser procedures. However, be that as it may, an examined eye may make involuntary eyeball movements during the acquisition of a UBM scan which can lead to an inaccurate so-called outlier UBM scan in comparison to a UBM scan acquired when an examined eye is correctly fixated. To overcome the problem of gaze stability, various eye tracking methods have been developed using reflected light signals or anatomical markers on eye surfaces to detect outlier scans. The ophthalmic UBM apparatus of the present invention preferably detects outlier UBM scans by comparing a consecutive sequence of say 4 to 6 UBM scans of purportedly identical UBM scans of an examined eye acquired at the same clock time probe position. An outlier UBM scan is determined with respect to its overall deviation from a common pattern shared by the other UBM scans with which it is purportedly identical. The clinical application at hand defines the required level of identicalness with some clinical applications requiring more stringent outlier thresholds than others. More stringent outlier thresholds lead to more accurate ophthalmic information regarding an examined eye, however, higher identicalness accuracy typically requires more UBM scans at the same clock time probe position.

UBM probes acquire sector shaped UBM scans which are highly accurate centered around their focal planes and have a diminishing accuracy as a function of axial distance from their focal planes. The area of a UBM scan which is sufficient accurately for the purpose of constructing an accurate computerized vertical cross section of a fixated examined eye is a relatively narrow in focus truncated sector bordering both sides of the focal plane of the UBM probe acquiring the UBM scan. But the in focus truncated sector does not cover enough of a fixated examined eye's anterior segment for the intended purpose of the present invention. Accordingly, the ophthalmic UBM apparatus of the present invention includes a UBM examination height adjustment arrangement for adjusting an UBM examination height of the UBM scanner relative to the overhead fixation target for enabling acquisition of vertically spaced apart UBM scans of an examined eye at the same clock time probe positions. The UBM examination height adjustment arrangement preferably enables incremental height adjustments in the range of from about 250 μm to 500 μm as opposed to continuous height adjustments. Adjacent vertical spaced apart UBM scans at the same clock time probe position preferably have a small vertical overlap to prevent missing information therebetween. Increasing the overlap between two adjacent vertical spaced apart series of UBM scans leads to an increase in the number of vertical spaced apart series of UBM scans to construct computerized vertical cross sections.

One preferred embodiment of the ophthalmic UBM apparatus of the present invention includes a UBM scanner with a single UBM probe. Such ophthalmic UBM apparatus typically requires two vertical spaced apart series of UBM scans for constructing computerized vertical cross sections of anterior chambers only sufficient for constructing a computerized 3D model for the selection, design and positioning of ICLs only. The first series of UBM scans is preferably acquired with the UBM probe's focal plane at the midpoint of the UBM probe's scan path located on the anterior surface of an examined eye's iris. The second series of UBM scans is typically acquired one millimeter below the first series of UBM scans.

Another preferred embodiment of the present invention includes a UBM scanner with a UBM probe pair equidistanced from the vertical UBM examination centerline in a fixed mechanical arrangement and rotatable therearound, thereby halving the number of rotational displacements about the vertical UBM examination centerline to acquire UBM scans at the same number of clock time probe positions in comparison to a single UBM probe. But the intended purpose of ophthalmic UBM apparatus with a UBM probe pair as opposed to a single UBM probe is not to save examination time but rather completely eliminate any error between vertical UBM scans acquired at diametric clock time probe positions. By virtue of a fixed mechanical arrangement between the UBM probe pair, the ophthalmic UBM apparatus can acquire absolutely diametric UBM scans over its entire lifetime. Such diametric UBM scans enable constructing highly accurate computerized vertical cross sections of full anterior segments including both their anterior chamber and their posterior chamber for constructing a highly accurate computerized 3D model of an anterior segment for the selection, design and positioning of pseudophakic IOLs and accommodating IOLs. Such computerized vertical cross sections are constructed from multiple vertical spaced apart series of UBM scans to improve the accuracy of the computerized 3D model which can approach the axial resolution and lateral resolution of the UBM probes acquiring the UBM scans.

The ophthalmic UBM apparatus of the present invention is designed to minimize electromagnetic and electrostatic interference particularly during acquisitions of UBM scans. One design feature is that a UBM transducer is not directly reciprocated by a motor but rather via a transmission arrangement thereby enabling distancing the motor from the UBM transducer. Another design feature is that rotation of the UBM scanner with a single UBM probe employs a maximal ±180° half turn rotation relative to a set-up position as opposed to a maximal 360° full turn rotation to simplify the electrical wiring of the ophthalmic UBM apparatus of the present invention.

The ophthalmic UBM apparatus of the present invention can be readily implemented with future UBM scanning technologies currently undergoing development. Exemplary developments include inter alia reducing the size of UBM transducers, constructing micro UBM transducer arrays, and scanning methods.

BRIEF DESCRIPTION OF DRAWINGS

In order to understand the invention and to see how it can be carried out in practice, preferred embodiments will now be described, by way of non-limiting examples only, with reference to the accompanying drawings in which similar parts are likewise numbered, and in which.

DETAILED DESCRIPTION OF PREFERRED EMBODIMENTS OF THE INVENTION

Ophthalmic UBM Apparatus with UBM Scanner with Single UBM Probe

Figure 1:
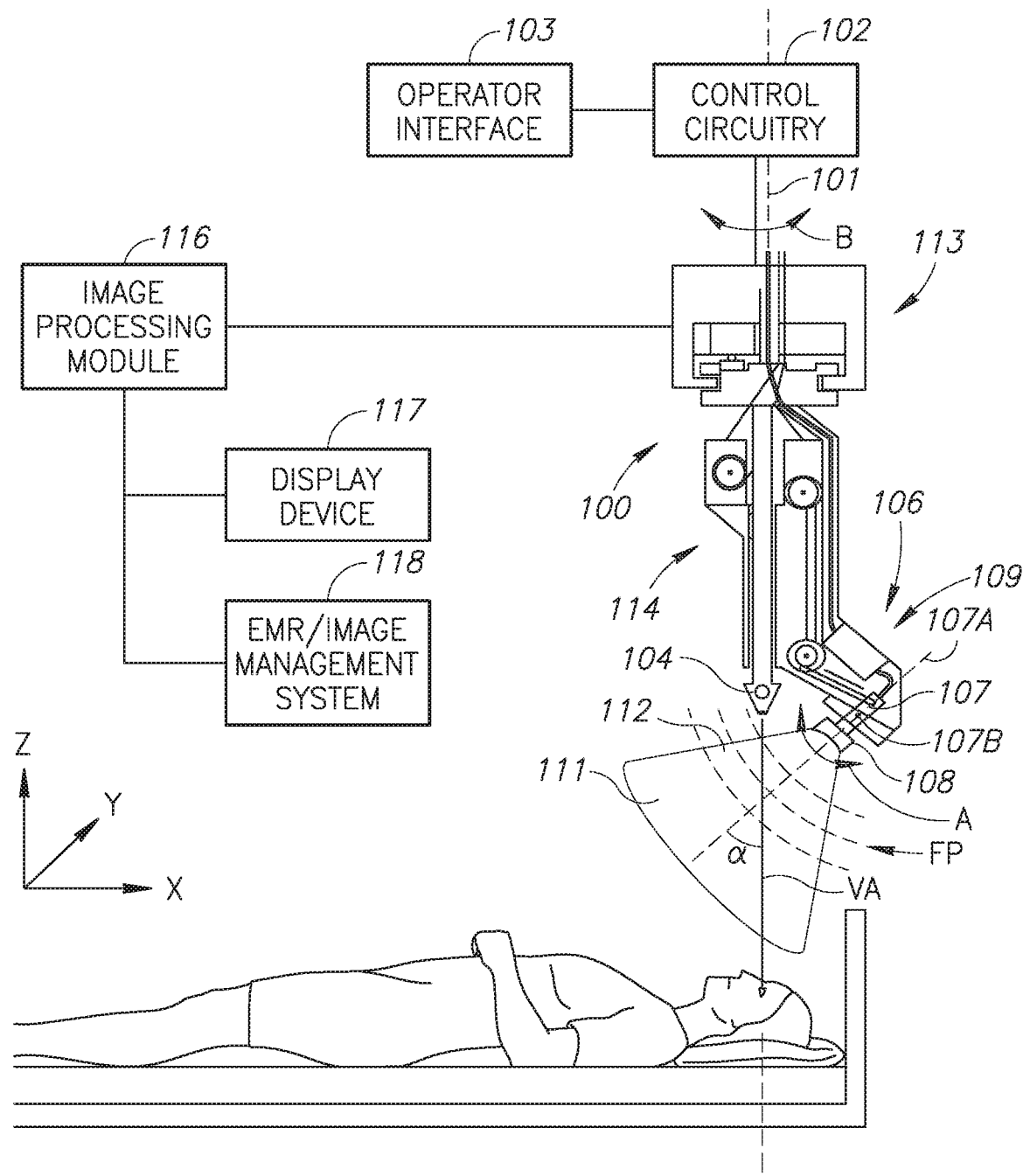
FIG. 1 is a combined side elevation view and block diagram of ophthalmic UBM apparatus including a vertical UBM examination centerline and a UBM scanner with a single UBM probe for examining a human eye.

FIG. 1 shows ophthalmic UBM apparatus 100 for conducting an UBM examination on a human patient in a supine position and a reference coordinate system including a X-Y horizontal plane, a X-Z vertical plane and a Y-Z vertical plane. The ophthalmic UBM apparatus 100 includes a vertical UBM examination centerline 101 parallel to the Y-axis. The patient's head is required to be supported for stabilization purposes. The patient has an open contact cup placed on his eye to be examined and filled with a liquid or gel medium.

The ophthalmic UBM apparatus 100 includes control circuitry 102 including an operator interface 103 for operating same and acquires vertical UBM scans to construct computerized vertical cross sections therefrom, and a computerized 3D model of anterior segments for a wide range of ophthalmic clinical applications. The computerized cross sections and the computerized 3D models can be subsequently used for determining intraocular anatomical measurements at the required clinical accuracy for correctly fitting intraocular lens, for example, sulcus to sulcus diameter, and the like.

The ophthalmic UBM apparatus 100 includes an illuminated overhead fixation target 104 along the UBM examination centerline 101 for fixating an examined eye's visual axis VA co-axial therewith. A patient is placed relative to the ophthalmic UBM apparatus 100 such that the overhead fixation target 104 is deployed immediately above an examined eye for direct fixation of its visual axis defined as an imaginary straight line between the fixation target 104 and the eye's fovea. The overhead fixation target 104 is illuminated such that a patient can readily direct gaze theretoward without having to try to focus thereon. Suitable illuminated fixation targets 104 include a LED, and the like. The LED itself can be directly deployed in front of an examined eye. Or preferably an optical fiber arrangement can be employed for transmitting LED light from a remote LED to directly in front of an examined eye.

The ophthalmic UBM apparatus 100 includes a UBM scanner 106 including a UBM probe 107 having a known spatial position with respect to the overhead fixation target 104. The UBM probe 107 has a UBM probe axis 107A directed towards the UBM examination centerline 101 and subtending an acute included angle α therewith in the side elevation view. The included angle α is typically in the range of 45°±10°.

The UBM probe 107 has a UBM transducer 108 with a fixed focal plane FP and a motorized probe arrangement 109 for reciprocating the UBM transducer 108 along a predetermined scan path lateral to the UBM examination centerline 101 to avoid the UBM transducer 108 intercepting the examined eye's direct fixation on the overhead fixation target 104. Suitable conventional scan paths include inter alia a curved scan path, a linear scan path, and the like. The UBM probe 107 reciprocates the UBM transducer 108 about a UBM probe pivot 107B along a curved scan path denoted A such that the UBM probe 107 scans a sector shaped vertical UBM scan 111 in a plane passing through the UBM examination centerline 101. The UBM transducer 108 is shown in its midway position along its reciprocation stroke. The sector shaped vertical UBM scan 111 includes a narrow in focus truncated sector 112 on both sides of the focal plane FP.

Figure 2:
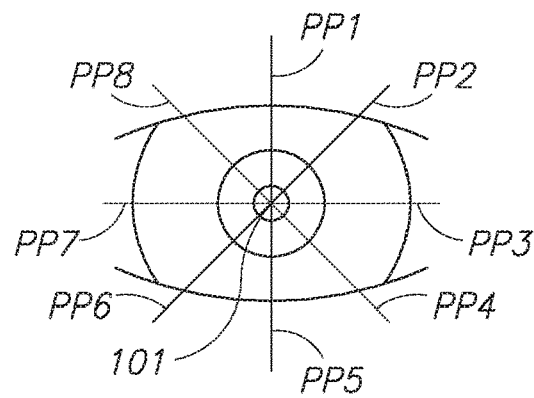
FIG. 2 is a schematic view showing eight clock time probe positions equispaced around an UBM examination centerline.

The ophthalmic UBM apparatus 100 includes a motorized UBM scanner rotation arrangement 113 for selectively rotating the UBM scanner 106 around the UBM examination centerline 101 as denoted by arrow B to an annular set of predetermined clock time probe positions PP preferably equispaced around the UBM examination centerline 101 such that the UBM probe 107 effectively sweeps out a cone with the overhead fixation target 104 at its apex. FIG. 2 shows eight clock time probe positions PP1, PP2, . . . , PP8 corresponding to 12:00, 01:30, 03:00, 04:30, 06:00, 07:30, 09:00 and 10:30. The diametric clock time probe positions 12:00 and 06:00 correspond to a sagittal cross section of a fixated examined eye. The diametric clock time probe positions 09:00 and 03:00 correspond to a transverse cross section of a fixated examined eye.

The UBM probe 107 can optionally include an additional axis for deploying the UBM transducer 108 such that the motorized probe arrangement 109 reciprocates the UBM transducer 108 in an inclined plane relative to the UBM examination centerline 101.

The ophthalmic UBM apparatus 100 includes a motorized UBM examination height adjustment arrangement 114 for selectively adjusting an UBM examination height H of the UBM scanner 106 relative to the overhead fixation target 105 for enabling scanning the examined eye at spaced apart UBM examination heights. The motorized UBM examination height adjustment arrangement 114 preferably adjusts the UBM examination height of the UBM scanner 106 relative to the overhead fixation target 104 in predetermined incremental height adjustments of between about 250 µm to 500 µm.

Figure 3:
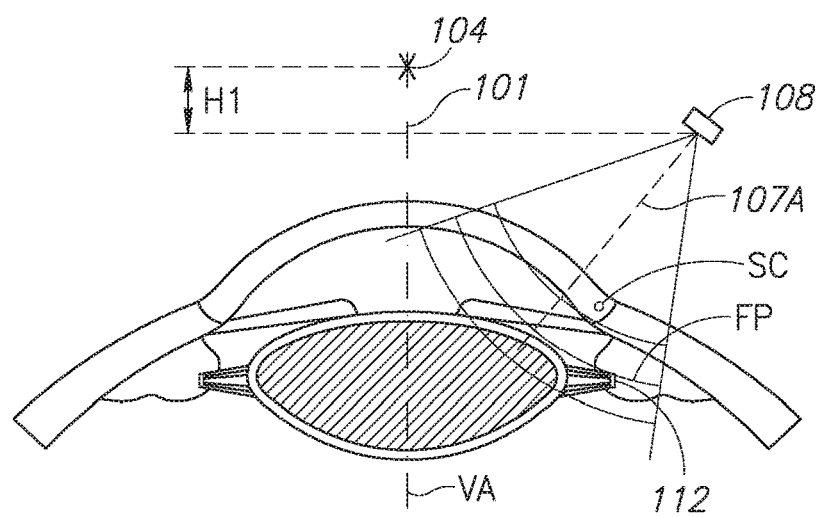
FIG. 3 is a schematic view showing a transverse cross section of an examined eye and the UBM probe at a 03:00 clock time probe position at an initial UBM examination height H1 relative to the overhead fixation target.
Figure 4:
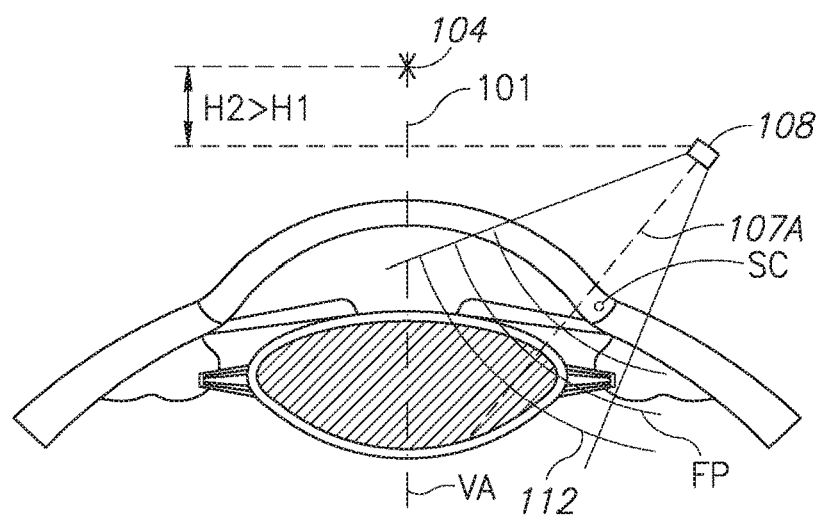
FIG. 4 is a schematic view similar to FIG. 3 with the UBM probe at a subsequent UBM examination height H2 relative to the overhead fixation target where H2>H1.

FIG. 3 and FIG. 4 show the use of the ophthalmic UBM apparatus 100 for acquiring UBM scans for constructing computerized vertical cross sections for constructing a computerized 3D model of a posterior chamber suitable for implantation of an ICL. FIG. 3 shows the UBM scanner 106 set at an initial UBM examination height H1 relative to the overhead fixation target 104 such that its UBM probe's focal plane FP at the midpoint of the UBM probe's scan path A is located on the anterior surface of the examined eye's iris. FIG. 4 shows the UBM scanner 106 set about one millimeter below the first series of UBM scans.

The ophthalmic UBM apparatus 100 can be equally provisioned with a UBM probe 108 with a high ultrasound frequency for imaging eye wall structures, for example, Schlemm's canal denoted SC, and the like. In such case, the UBM probe 108 is deployed closer to an examined eye than compared to a UBM probe 108 for posterior chamber imaging.

The ophthalmic UBM apparatus 100 includes an image processing module 116 for processing UBM scans and displaying computerized vertical cross sections, computerized 3D models, and the like, on a display device 117. The ophthalmic UBM apparatus 100 can also be connected to Electronic Medical Record (EMR) or image management system 118 for archive purposes.

The control circuitry 102 enables the setting of several scanning and image processing parameters as follows: First, the control circuitry 102 enables operator setting of the UBM transducer's scan angle upto a typical 35° maximum scan angle. Second, the control circuitry 102 enables operator setting of the number of probe positions at which scans are to be acquired. Increasing the number of probe positions prolongs an eye examination and increases the accuracy of the ophthalmic information which can be determined regarding an examined eye. Third, the control circuitry 102 enables operator setting of the number of UBM examination heights at which UBM scans are to be acquired. Increasing the number of UBM examination heights prolongs an examination and increases the accuracy of the ophthalmic information which can be determined regarding an examined eye. Fourth, the control circuitry 102 enables operator setting of an outlier threshold for determining whether a UBM scan of an examined eye was instantaneously acquired when the examined eye was fixated on the fixation target. And fifth, the control circuitry 102 enables operator setting of the number of UBM scans to be averaged at a single clock time probe position PP.

The operation of the ophthalmic UBM apparatus 100 as follows:

Position the human subject in a supine position and request the subject to look directly upward. Place an open contact cup on the subject's eye to be examined and fill with physiological fluid, for example, balanced saline solution.

Position the overhead fixation target over the eye to be examined such that the patient can align the line of sight of his eye to be examined directly at the overhead fixation target for aligning his eye's visual axis co-axial with the UBM examination centerline.

Set up the ophthalmic UBM apparatus according to a predetermined examination protocol in terms of the number of clock time probe positions, the number of UBM examination heights at which UBM scans are to be acquired, outlier threshold, and the like.

The UBM scanner typically acquires four or five UBM scans of an examined eye at a single clock time probe position. The image processing module processes the UBM scans on the fly to determine outlier UBM scans, if any. The image processing module averages two of more of non-outlier scans of the examined eye at a single clock time probe position.

The ophthalmic UBM apparatus rotates the UBM scanner to the next clock time probe position and repeats the above steps for the next clock time probe position. The ophthalmic UBM apparatus repeats the above steps for all the clock time probe positions at an initial UBM examination height relative to the overhead fixation target.

The ophthalmic UBM apparatus adjusts the UBM examination height of the UBM scanner relative to the overhead fixation target and repeats the above steps for the new UBM examination height.

After acquisition of the required UBM scans at the required UBM examination heights of the UBM scanner, the image processing module processes the UBM scans acquired at the same clock time probe positions and at the diametric clock time probe positions at the two or more UBM examination heights to initially construct computerized vertical segment cross sections.

Thereafter, the imaging processing module constructs a computerized 3D model from the computerized vertical cross sections. The image processing module can display same on the display device and additionally determine ophthalmic information regarding the examined eye, for example, intraocular anatomical measurements, and the like.

Figure 5:
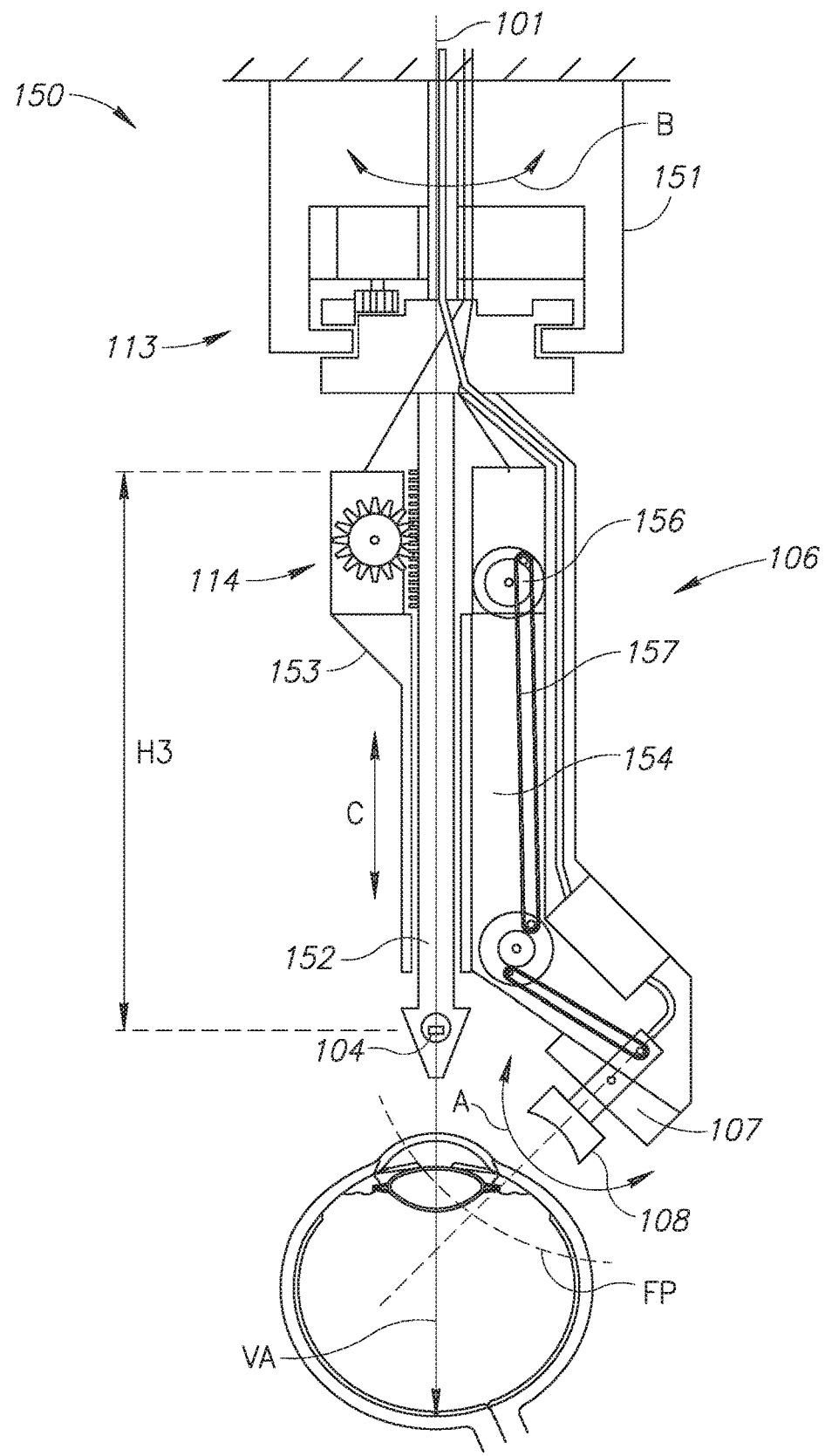
FIG. 5 is a schematic view of a preferred embodiment of ophthalmic UBM apparatus with a UBM scanner with a single UBM probe for examining a left eye at an initial UBM examination height.
Figure 6:
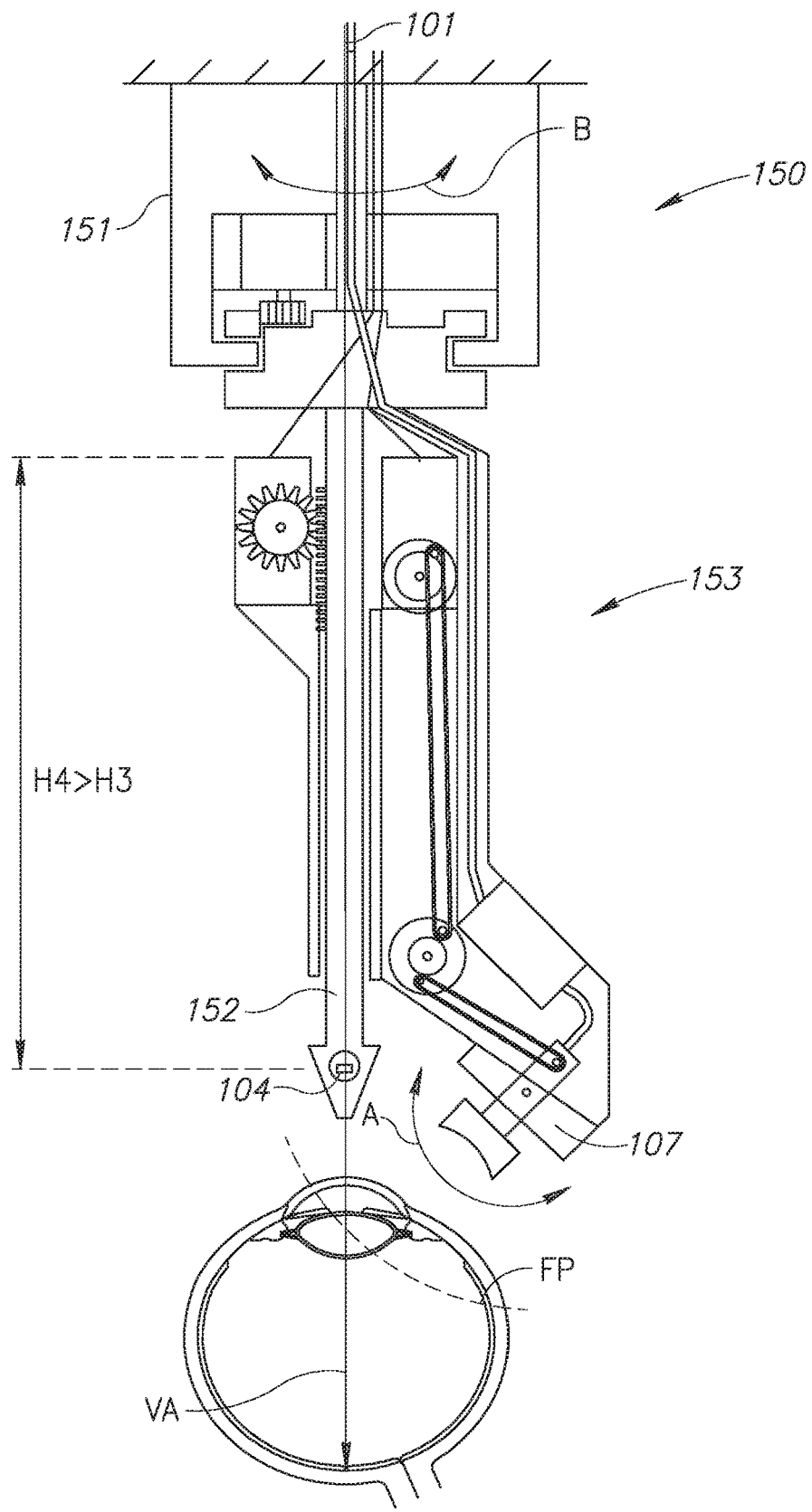
FIG. 6 is a schematic view of FIG. 5's ophthalmic UBM apparatus for examining the left eye at a subsequent UBM examination height.
Figure 7:
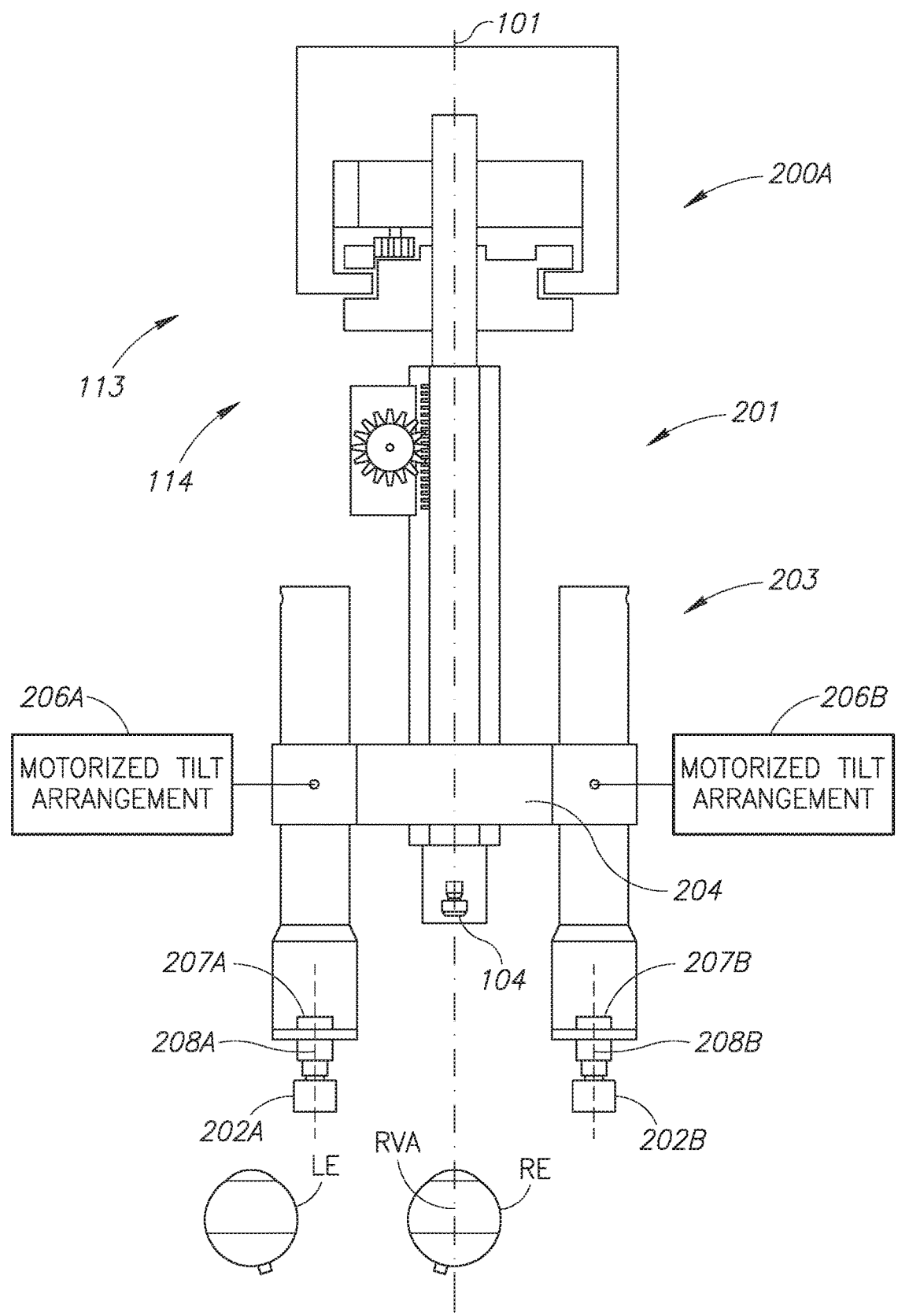
FIG. 7 is a schematic representation of a first embodiment of ophthalmic UBM apparatus including a UBM scanner with a UBM probe pair for examining a right eye.
Figure 8:
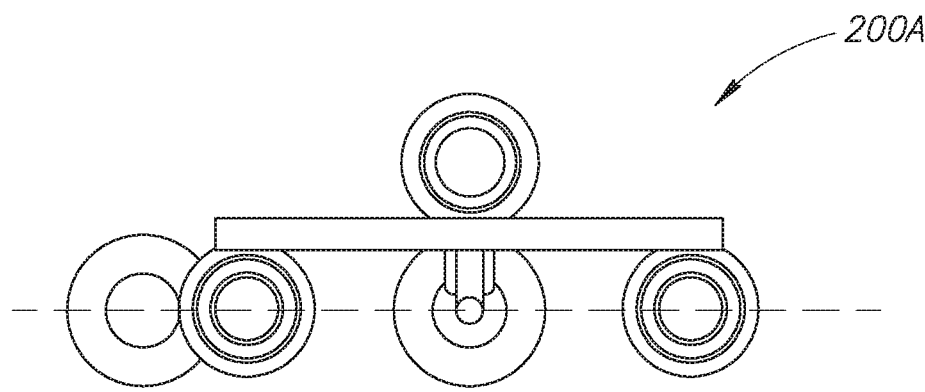
FIG. 8 is a schematic top plan view of FIG. 7's ophthalmic UBM apparatus.
Figure 9:
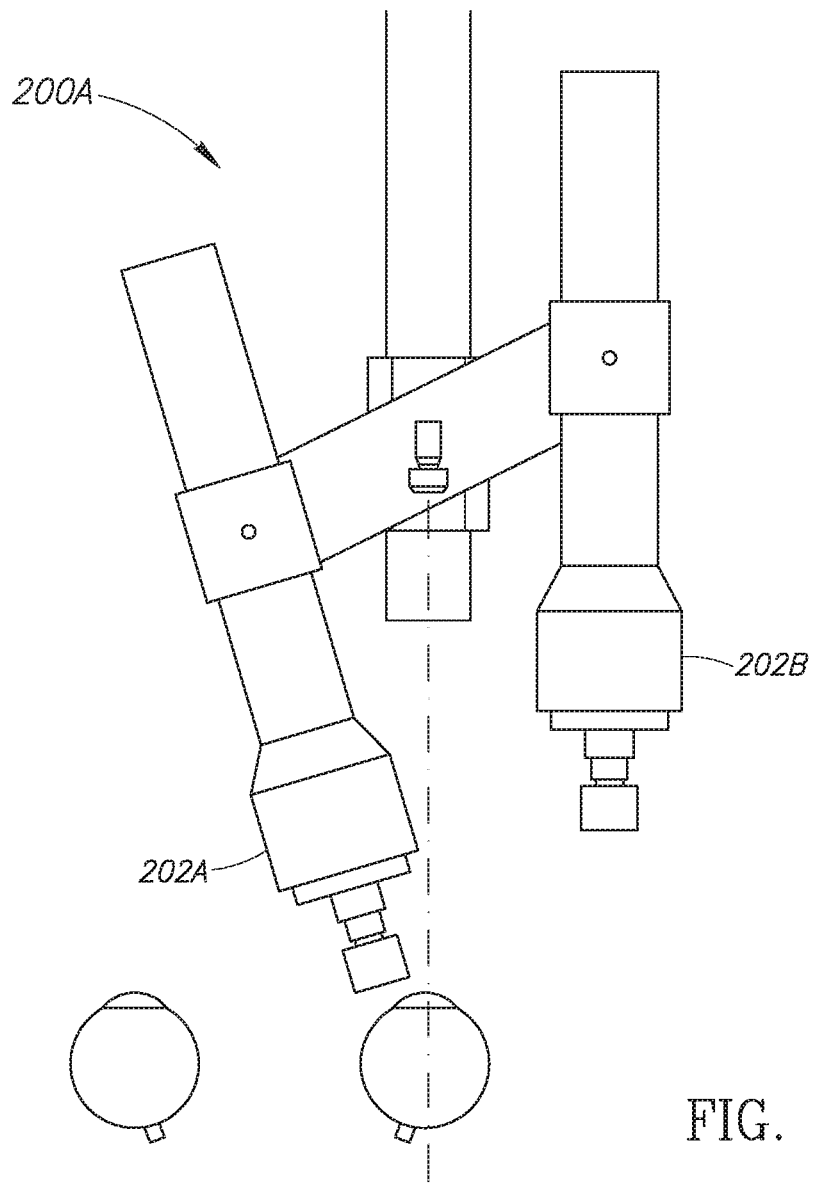
FIG. 9 is a schematic front elevation view of FIG. 7's ophthalmic UBM apparatus with its first UBM probe in an operative scan acquisition position for scanning the right eye and its second UBM probe in a retracted non-scan acquisition position.
Figure 10:
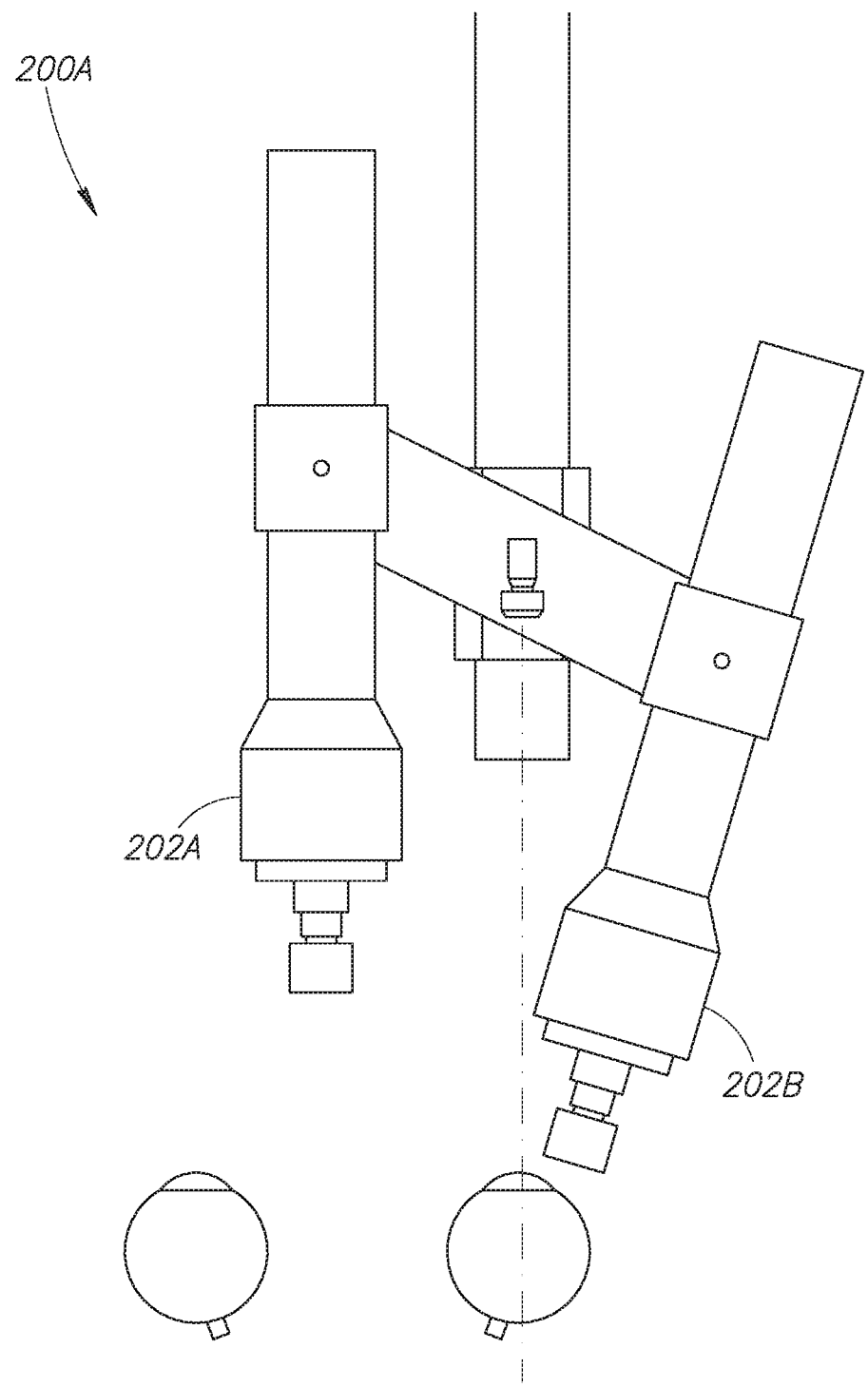
FIG. 10 is a schematic front elevation view of FIG. 7's ophthalmic UBM apparatus with its first UBM probe in a retracted non-scan acquisition position and its second UBM probe in an operative scan acquisition position for scanning the right eye.
Figure 11:
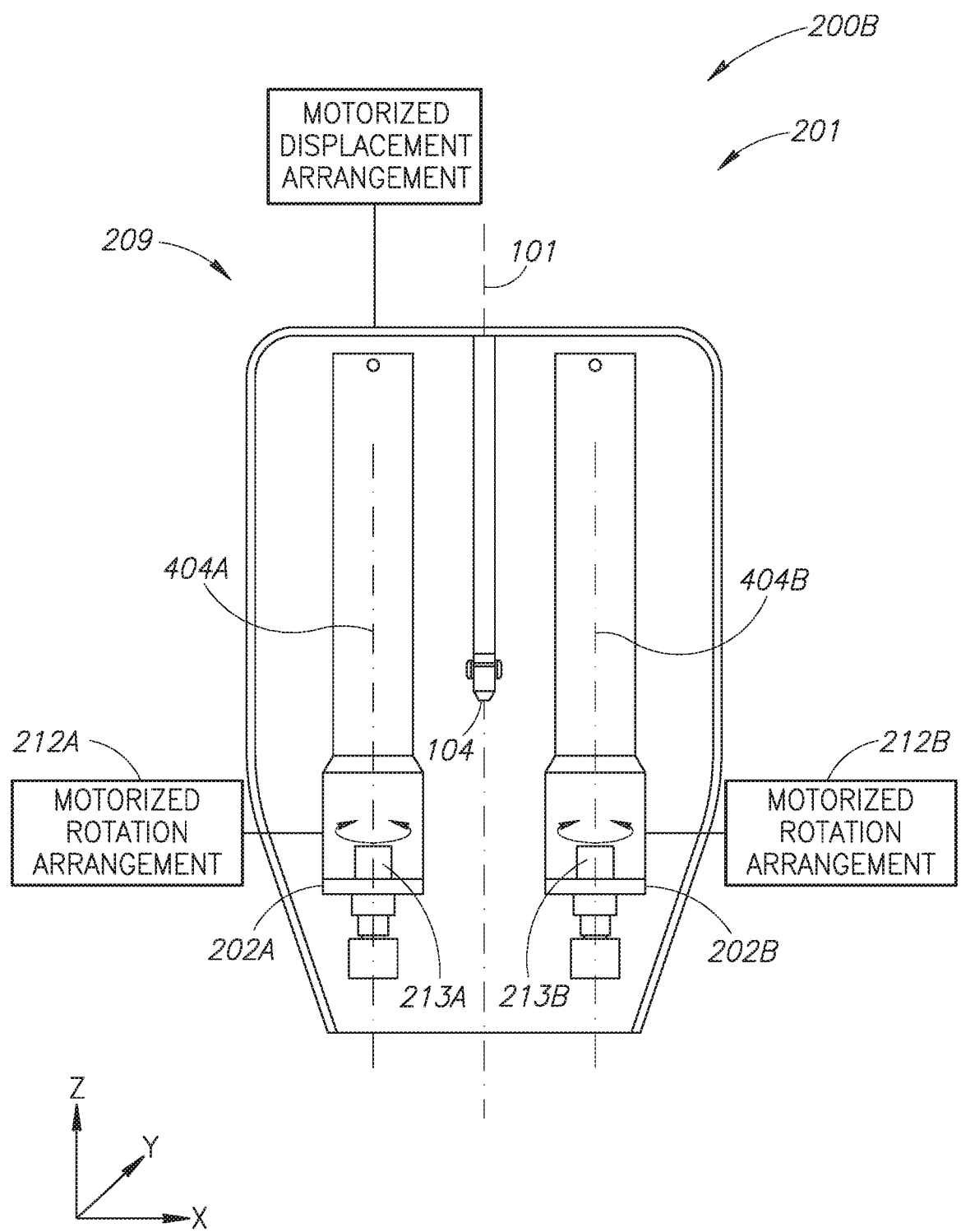
FIG. 11 is a schematic representation of a second embodiment of ophthalmic UBM apparatus with a UBM scanner with a UBM probe pair in a set up position for conducting UBM examinations.
Figure 12:
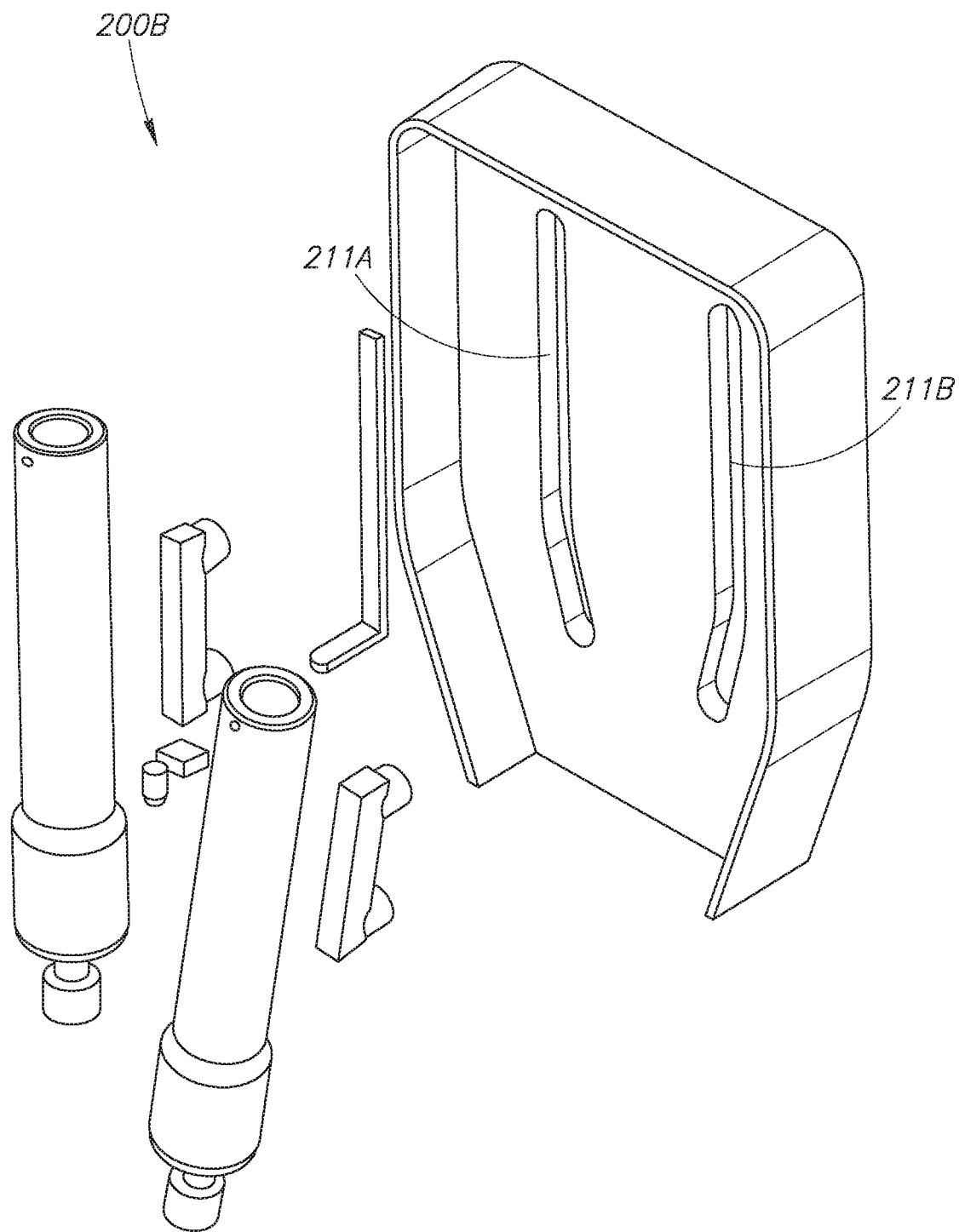
FIG. 12 is an exploded view of FIG. 11's ophthalmic UBM apparatus.
Figure 13:
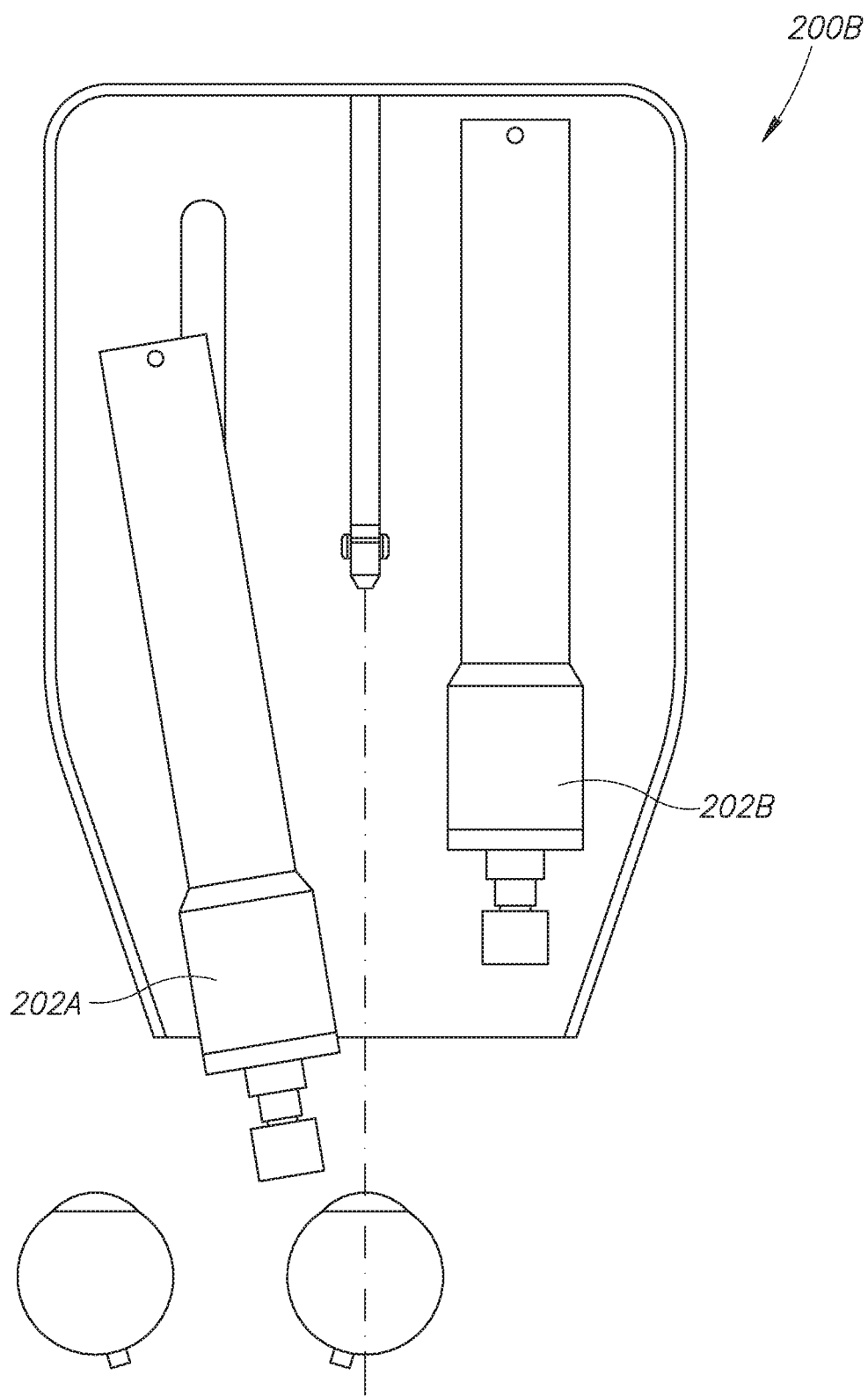
FIG. 13 is a schematic front elevation view of FIG. 11's ophthalmic UBM apparatus with its first UBM probe in an operative scan acquisition position for scanning a right eye and its second UBM probe in a retracted non-scan acquisition position.
Figure 14:
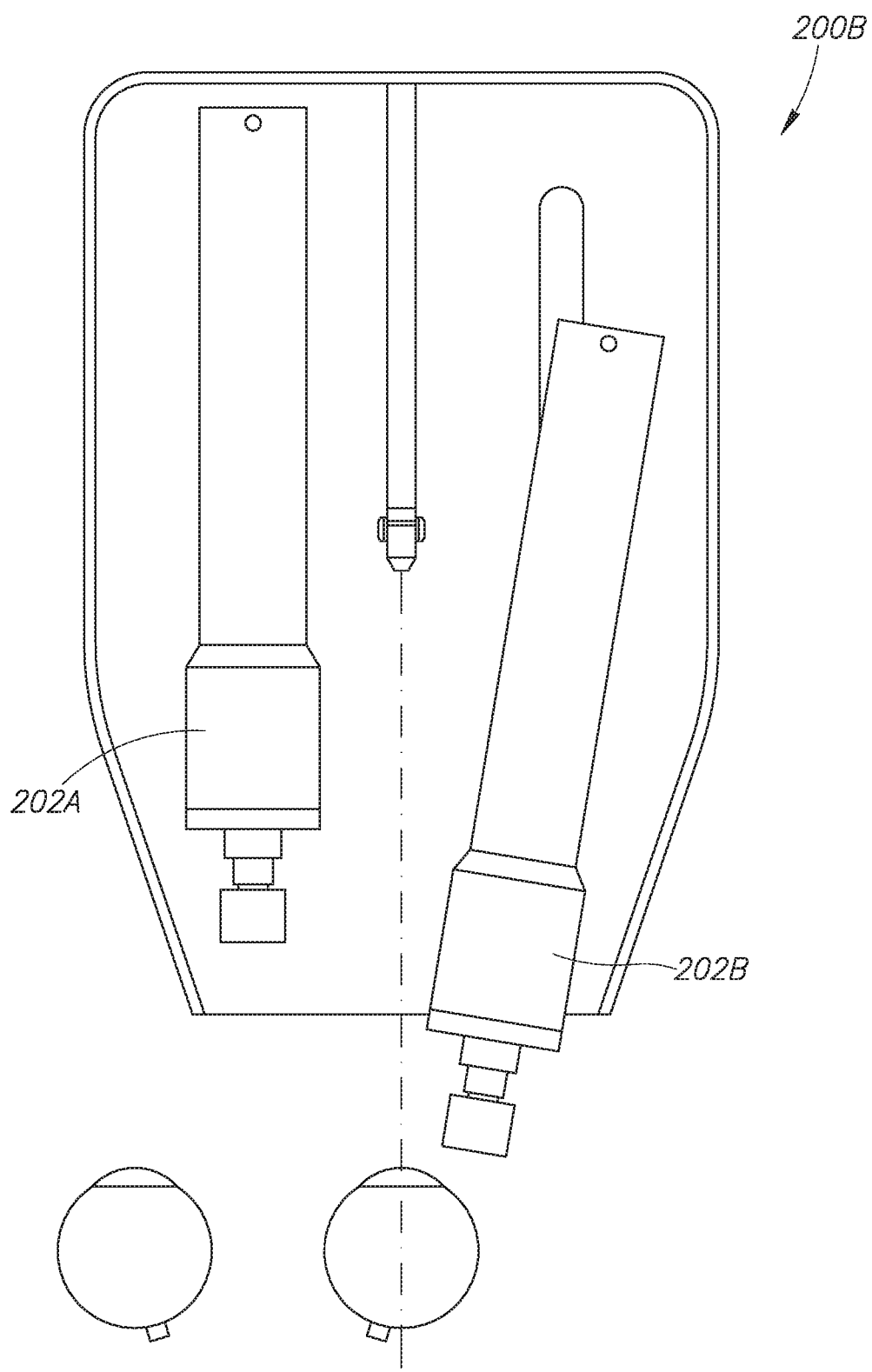
FIG. 14 is a schematic front elevation view of FIG. 11's ophthalmic UBM apparatus with its first UBM probe in a retracted non-scan acquisition position and its second UBM probe in an operative scan acquisition position for scanning the right eye.

FIG. 5 and FIG. 6 show one preferred embodiment 150 of the ophthalmic UBM apparatus 100 and therefore similar parts are likewise numbered. The ophthalmic UBM apparatus 150 includes an overhead housing 151 having a motorized UBM scanner rotation arrangement 113 with a downward depending support 152 co-axial with the UBM examination centerline 101. The motorized UBM scanner rotation arrangement 113 selectively rotates the downward depending support 152 to an annular set of predetermined clock time probe positions around the UBM examination centerline 101. The downward depending support 152 terminates at the illuminated overhead fixation target 104.

The ophthalmic UBM apparatus 150 includes a UBM scanner housing 153 mounted on the downward depending support 152. The UBM scanner housing 153 accommodates the UBM examination height adjustment arrangement 114 and the UBM scanner 106. The UBM examination height adjustment arrangement 114 adjusts the displacement of the UBM scanner housing 153 along the downward depending support 152 thereby adjusting the UBM examination height of the UBM scanner 106 relative to the overhead fixation target 104, and correspondingly an examined eye.

The UBM scanner 106 includes a sealed transmission housing 154 accommodating the motorized probe arrangement 109 for reciprocating the UBM transducer 108. The motorized probe arrangement 109 includes a motor 156 and a transmission arrangement 157 for transmitting motion from the motor 156 to the UBM probe 107. The transmission arrangement 157 distances the UBM transducer 108 from the motor 156 to minimize interference during operation of the UBM probe 107 to scan an examined eye.

FIG. 5 shows the ophthalmic UBM apparatus 150 at an initial UBM examination height H3 relative to the overhead fixation target 104 and FIG. 6 shows the ophthalmic UBM apparatus at a subsequent UBM examination height H4 relative to the overhead fixation target H4 where H4>H3, namely, deployed further from the examined eye.

Ophthalmic UBM Apparatus with UBM Scanner with UBM Probe Pair

FIGS. 7 to 10 show ophthalmic UBM apparatus 200A and FIGS. 11 to 14 show ophthalmic UBM apparatus 200B both similar in construction and operation as the ophthalmic UBM apparatus 100 and therefore similar parts are likewise numbered. Thus, both ophthalmic UBM apparatus 200A and ophthalmic UBM apparatus 200B include an UBM examination centerline 101, an illuminated overhead fixation target 104, a motorized UBM scanner rotation arrangement 113, a motorized UBM examination height adjustment arrangement 114, and an image processing module 116.

The ophthalmic UBM apparatus 200 differ from ophthalmic UBM apparatus 100 insofar the latter 200 include a UBM scanner 201 having a UBM probe pair 202 including a first UBM probe 202A and a second UBM probe 202B diametrical equidistanced with respect to the UBM examination centerline 101. Accordingly, the ophthalmic UBM apparatus 200 requires half the number of rotational steps of the UBM scanner 201 relative to the UBM scanner 106 for acquiring UBM scans at the same clock time probe positions. However, because of the size of presently available UBM transducers, only a single UBM probe 202A or 202B of a UBM probe pair 202 can be deployed in a scan acquisition position at any one time.

The ophthalmic UBM apparatus 200 differ in terms of their mechanical arrangements for simultaneous deployment of the first UBM probe 202A at a scan acquisition position for scanning an examined eye and the second UBM probe 202B at a retracted non-scan acquisition position at a scanning position and subsequent simultaneous deployment of the first UBM probe 202A at a retracted non-scan acquisition position and the second UBM probe 202B at a scan acquisition position for scanning the examined eye at a clock time probe position.

FIGS. 7 to 10 show the ophthalmic UBM apparatus 200A includes a motorized UBM probe displacement arrangement 203 including a straight cross beam 204 pivotal on the UBM examination centerline 101 for alternatively reciprocating the UBM probes 202A and 202B between a retracted non-scan acquisition position and an operative scan acquisition position. The ophthalmic UBM apparatus 200A additionally includes motorized tilt arrangements 206A and 206B for correspondingly tilting the UBM probes 202A and 202B in an X-Z plane. The ophthalmic UBM apparatus 200A additionally includes motorized rotation arrangements 207A and 207B for correspondingly rotating the UBM probes 202A and 202B about rotation axes 208A and 208B.

FIGS. 11 to 14 show the ophthalmic UBM apparatus 200B includes a motorized UBM probe displacement arrangement 209 with a pair of guidance slots 211A and 211B for corresponding guided travel of the UBM probes 202A and 202B in an X-Z plane between their retracted non-scan acquisition positions and their operative scan acquisition positions. The ophthalmic UBM apparatus 200B additionally includes motorized rotation arrangements 212A and 212B for correspondingly rotating the UBM probes 202A and 202B about rotation axes 213A and 213B.

While the invention has been described with respect to a limited number of embodiments, it will be appreciated that many variations, modifications, and other applications of the invention can be made within the scope of the appended claims.

The invention claimed is:

1. Ophthalmic Ultrasound Bio-Microscope (UBM) apparatus for examining an eye of a human subject in a supine position, the ophthalmic UBM apparatus including a vertical UBM examination centerline, the ophthalmic UBM apparatus comprising:

(a) an illuminated overhead fixation target deployed along the vertical UBM examination centerline for direct fixation by the examined eye for fixating its visual axis therealong;

(b) a UBM scanner including a UBM probe having a UBM probe axis directed towards the examined eye, said UBM probe having a known spatial position with respect to said overhead fixation target, said UBM probe having a UBM transducer and a motorized probe arrangement for reciprocation of said UBM transducer along a predetermined scan path for acquiring a vertical UBM scan of the examined eye at a predetermined UBM examination height relative to the examined eye, said scan path being lateral to the UBM examination centerline to preclude said UBM transducer intercepting said direct fixation of the examined eye on said illuminated overhead fixation target;

(c) a motorized UBM scanner rotation arrangement for selectively rotating said UBM scanner around the UBM examination centerline to an annular set of predetermined clock time probe positions wherein said annular set of predetermined clock time positions includes at least one diametric pair of clock time probe positions;

(d) a motorized UBM examination height adjustment arrangement for selectively adjusting said UBM examination height of said UBM scanner relative to the examined eye to at least two predetermined UBM examination heights; and (e) an image processing module for processing said vertical UBM scans for determining ophthalmic information regarding the examined eye, said ophthalmic information including computerized vertical cross sections of at least an anterior chamber of an anterior segment of the examined eye wherein each computerized vertical cross section is constructed from UBM scans acquired at at least two diametric pair of clock time probe positions.

2. Apparatus according to claim 1 wherein said UBM scanner includes a single UBM probe and said motorized UBM scanner rotation arrangement rotates said UBM scanner a maximal ±180° half turn rotation with respect to the UBM examination centerline.

3. Apparatus according to claim 1 wherein said UBM scanner includes a UBM probe pair diametrically equidistanced from the UBM examination centerline in a fixed mechanical arrangement and a motorized UBM probe displacement arrangement enabling simultaneous deployment of a first UBM probe of said UBM probe pair at a scan acquisition position for scanning the examined eye and a second UBM probe of said UBM probe pair at a retracted non-scan acquisition position at a probe position of said annular set of predetermined probe positions and subsequent simultaneous deployment of said first UBM probe of said UBM probe pair at a retracted non-scan acquisition position and said second UBM probe of said UBM probe pair at a scan acquisition position for scanning the examined eye at said probe position of said annular set of predetermined probe positions.

4. Apparatus according to claim 3 wherein said motorized UBM probe displacement arrangement includes a straight cross beam pivotal at the UBM examination centerline for see-saw like reciprocation of said first UBM probe and said second UBM probe between their corresponding said scan acquisition position and said non-scan acquisition position.

5. Apparatus according to claim 3 wherein said motorized UBM probe displacement arrangement includes a pair of guidance slots diametrically equidistanced with respect to the UBM examination centerline for guided travel of said first UBM probe and said second UBM probe between their corresponding said scan acquisition position and said non-scan acquisition position.

6. Apparatus according to claim 1 wherein said motorized UBM scanner rotation arrangement simultaneously rotates said motorized UBM examination height adjustment arrangement and said UBM scanner to said annular set of predetermined clock time probe positions.

7. Apparatus according to claim 1 wherein said motorized UBM examination height adjustment arrangement adjusts said UBM examination height of said UBM scanner relative to the overhead fixation target in incremental height adjustments.

8. Apparatus according to claim 1 wherein said motorized probe arrangement includes a motor and an elongated transmission arrangement for indirect transmission of motion of said motor to said UBM transducer for reciprocation of said UBM transducer along said scan path.

9. Apparatus according to claim 1 wherein said image processing module compares a series of at least three UBM scans of said UBM probe at a clock time probe position for identifying an outlier UBM scan according to a predetermined outlier threshold.

10. Apparatus according to claim 9 wherein said image processing module averages at least two non-outlier UBM scans acquired at a clock time probe position for determining ophthalmic information.

* * * * *